United States Patent
Kong et al.

(10) Patent No.: US 11,975,089 B2
(45) Date of Patent: May 7, 2024

(54) COMPOSITION FOR CONDITIONING KERATIN FIBERS

(71) Applicant: L'OREAL, Paris (FR)

(72) Inventors: Lingchao Kong, Shanghai (CN); Wi-Soon Chia, Shanghai (CN); Maxime De Boni, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/957,434

(22) PCT Filed: Dec. 28, 2017

(86) PCT No.: PCT/CN2017/119396
§ 371 (c)(1),
(2) Date: Jun. 24, 2020

(87) PCT Pub. No.: WO2019/127214
PCT Pub. Date: Jul. 4, 2019

(65) Prior Publication Data
US 2020/0330351 A1    Oct. 22, 2020

(51) Int. Cl.
| | |
|---|---|
| A61K 8/42 | (2006.01) |
| A61K 8/34 | (2006.01) |
| A61K 8/362 | (2006.01) |
| A61K 8/365 | (2006.01) |
| A61K 8/37 | (2006.01) |
| A61K 8/41 | (2006.01) |
| A61K 8/73 | (2006.01) |
| A61Q 5/12 | (2006.01) |

(52) U.S. Cl.
CPC ............... *A61K 8/42* (2013.01); *A61K 8/342* (2013.01); *A61K 8/362* (2013.01); *A61K 8/365* (2013.01); *A61K 8/37* (2013.01); *A61K 8/41* (2013.01); *A61K 8/73* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| | | | | |
|---|---|---|---|---|
| 5,997,854 | A * | 12/1999 | von Mallek | A61K 8/416 424/70.19 |
| 2002/0090348 | A1* | 7/2002 | Khoshdel | A61K 8/738 424/70.11 |
| 2004/0208837 | A1 | 10/2004 | Krueger et al. | |
| 2014/0348927 | A1* | 11/2014 | Schroeder | A61K 8/42 510/122 |
| 2016/0008261 | A1* | 1/2016 | Fields Taylor | A61K 8/31 424/59 |
| 2016/0296439 | A1 | 10/2016 | Iftikhar et al. | |

FOREIGN PATENT DOCUMENTS

| | | |
|---|---|---|
| CN | 1512871 A | 7/2004 |
| CN | 104548548 A | 4/2015 |
| CN | 104994832 A | 10/2015 |
| CN | 105380831 A | 3/2016 |
| CN | 105560076 A | 5/2016 |
| CN | 105764480 A | 7/2016 |
| WO | WO2014100970 * | 7/2014 |

OTHER PUBLICATIONS

Schaefer, Katie; Conditioning Agents for Hair Formulations, Cosmetics & Toiletried, Oct. 30, 2008, https://www.cosmeticsandtoiletries.com/formulating/function/moisturizer/11052451.html (Year: 2008).*
Salon Sorbet, Ingredient Love—Coco Caprylate/caprate, Jun. 23, 2014, https://salonsorbet.wordpress.com/2014/06/23/ingredient-love-coco-caprylatecaprate/ (Year: 2014).*
International Search Report and Written Opinion dated Sep. 20, 2018 in PCT/CN2017/119396 filed on Dec. 28, 2017.
Office Action dated May 22, 2021, in corresponding Brazilian Application No. BR112020010439-6.
Extended European Search Report dated Jul. 14, 2021, in European Patent Application No. 17936148.
Office Action dated Jun. 21, 2022, in corresponding Chinese Patent Application No. 201780097950.2 (with machine English Translation).
Office Action dated Oct. 17, 2022, in corresponding Korean Patent Application No. 10-2020-7021333 (with English-language Translation).
Office Action dated Apr. 24, 2023, in corresponding Korean Patent Application No. 10-2020-7021333, 2 pages.

* cited by examiner

*Primary Examiner* — Jennifer A Berrios
(74) *Attorney, Agent, or Firm* — Oblon, McClelland, Maier & Neustadt, L.L.P.

(57) ABSTRACT

A composition for conditioning keratin fibers, comprising: (a) at least one ($C_{10}$-$C_{30}$)alkylamido($C_1$-$C_8$)alkyl(di)($C_1$-$C_6$)alkylamine and their cosmetic salts and their solvates such as hydrates; (b) at least one dicarboxylic acid containing at least one hydroxyl group, preferably two hydroxyl groups, the said dicarboxylic acid not bearing a cyclic group; (c) at least one oil from eater of $C_6$-$C_{20}$ fatty acid and $C_6$-$C_{20}$ fatty alcohol; The composition provides to the keratin fibers, in particular the hair, an improved disentangling, and smoothness sensory.

11 Claims, No Drawings

COMPOSITION FOR CONDITIONING KERATIN FIBERS

FIELD OF THE INVENTION

The present invention relates to a composition in cosmetic field, such as composition for caring for keratin fibers, more particularly for conditioning keratin fibers, in particular the hair. The invention also relates to a cosmetic process for caring for keratin fibers, in particular the hair, using the composition of the present invention.

BACKGROUND OF THE INVENTION

Keratin fibers, in particular the hair is cleansed and treated with many cosmetic regiments to improve its look, color, style, etc. These various regiments however can remove the hair's natural oils and impart structural damage to the hair. For instance, shampooing is used primarily to cleanse the hair. Shampoos are often formulated with anionic surfactants that primarily clean as opposed to condition the hair. Anionic surfactants are highly effective for removing dirt, pollution, build-up, etc., from the hair, but they also remove sebum, a naturally occurring oily or waxy matter that automatically lubricates hair.

Shampooing can therefore leave the hair with a dry or coarse texture. Furthermore, thoroughly cleansed hair can become extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing properties of dry hair remain poor, and the hair has undesirable electrostatic properties in a low humidity atmosphere that causes the hair to "fly away" thereby further reducing the brushing properties of the hair.

Chemical hair treatments can further eliminate hair's natural oils (e.g., sebum) and alter the hair fiber's chemical and physical properties. The process of permanently changing the color of hair can involve depositing an artificial color onto the hair which provides a different shade or color to the hair. The process of lifting the color of hair requires the use of harsh chemicals such as alkalizing chemicals. These chemicals cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

There are many techniques and compositions for styling or altering the shape of hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While chemically treating hair can impart desirable cosmetic changes to the hair (e.g., change the color, shape, etc.), these chemical treatments can damage the hair fibers, in some cases even more than repeated shampooing of the hair. Like shampooing, chemical treatments can leave the hair dry with a coarse texture.

Conditioning compositions are used to improve or return to the hair its natural luster, shine, smoothness, and softness, for example, after shampooing the hair and/or after subjecting the hair to a chemical treatment. Conditioning compositions are often applied as rinses, cream-like emulsions, or lotions, and typically include one or more cationic compound. When used with shampooing, the commonly accepted method for conditioning the hair has been to shampoo the hair, followed by rinsing the hair, and then applying a conditioner composition, optionally followed by a second rinse. This improves the wet combing properties of the hair often because the conditioner composition coats the hair shaft and causes individual hair fibers in to resist tangling and matting because of the conditioner residue retained on the hair shaft.

It is known that various conditioning agents may provide different desired benefits. Conventional conditioning agents contain for example, cationic surfactants, silicones, and oils. Among which, cationic surfactants are widely used as a conditioning agent. The ability of this kind of cationic surfactants to provide conditioning effect to hair is attributable to the hydrophobic nature of the alkyl chain as well as to the cationic charge of the polar head group. The most popular cationic surfactants known are quaternary ammonium compounds containing in the molecule at least one long alkyl chain.

On the other hand, consumers show an increasing interest of cosmetic products with natural origin ingredients. Thus, products free of synthetic ingredients, such as silicones, the hair-treatment compositions, are more and more favored. Efforts have been made to formulate such compositions which deliver good cosmetic properties as those containing synthetic conditioning ingredients such as silicone oils.

However, it is still not satisfying. The inventors found it difficult to formulate compositions for conditioning the hair, that deliver very good conditioning effects, especially disentangling of hair, and smoothening the hair.

Meanwhile, these compositions are expected to be stable over time.

It is therefore an object of the present invention to provide a composition for caring for keratin fibers, in particular for conditioning the keratin fibers which possesses better conditioning effects, especially disentangling of both dry and wet hair and meanwhile, smoothening the hair.

Besides, it is also the aim of the present invention to provide a process for preparing a composition for conditioning keratin fibers.

SUMMARY OF THE INVENTION

The object of the present invention is achieved by a composition for conditioning keratin fibers, comprising: (a) at least one ($C_{10}$-$C_{30}$)alkylamido($C_1$-$C_8$)alkyl(di)($C_1$-$C_6$)alkylamine and their cosmetic salts and their solvates such as hydrates; (b) at least one dicarboxylic acid containing at least one hydroxyl group, preferably two hydroxyl groups, the said dicarboxylic acid not bearing a cyclic group; and (c) at least one oil selected from ester of $C_6$-$C_{20}$ fatty acid and $C_6$-$C_{20}$ fatty alcohol.

In another aspect, the present invention also relates to a use of the association of (a), (b), and (c):
 (a) at least one ($C_{10}$-$C_{30}$)alkylamido($C_1$-$C_8$)alkyl(di)($C_1$-$C_6$)alkylamine and their cosmetic salts and their solvates such as hydrates, preferably stearylamidopropyl dimethylamine;
 (b) at least one dicarboxylic acid containing at least one hydroxyl group, preferably two hydroxyl groups, the said dicarboxylic acid not bearing a cyclic group; and (c) at least one oil selected from ester of $C_6$-$C_{20}$ fatty acid and $C_6$-$C_{20}$ fatty alcohol. (a), (b), and (c) being used together for conditioning the keratin fibers, especially the hair.

Thus, the invention makes it possible to obtain a composition with excellent conditioning properties, especially disentangling of hair, and meanwhile providing smoothness to the hair. Moreover, the present invention also provides a composition which is eco-friendly by using biodegradable materials.

Lastly, the present invention is stable over time.

In the description, the terms "at least a" or "at least one" are equivalent to "one or more".

Other characteristics and advantages of the invention will emerge more clearly on reading the description and the examples that follow.

Preferably, the "keratin fiber" according to the present invention is the hair.

By "stable over time" we intend to mean a composition that does not undergo any significant change in its structure or properties for at least one month after its manufacture and especially for at least two months after its manufacture.

DETAILED DESCRIPTION OF THE INVENTION

The present invention is directed to a composition for conditioning keratin fibers, comprising:
(a) at least one $(C_{10}$-$C_{30})$alkylamido$(C_1$-$C_8)$alkyl(di)$(C_1$-$C_6)$alkylamine and their cosmetic salts and their solvates such as hydrates;
(b) at least one dicarboxylic acid containing at least one hydroxyl group, preferably two hydroxyl groups, the said dicarboxylic acid not bearing a cyclic group; and
(c) at least one oil selected from ester of $C_6$-$C_{20}$ fatty acid and $C_6$-$C_{20}$ fatty alcohol.

(a) $(C_{10}$-$C_{30})$alkylamido$(C_1$-$C_8)$alkyl (di)$(C_1$-$C_6)$alkylamine

The composition of the present invention comprises at least one $(C_{10}$-$C_{30})$alkylamido$(C_1$-$C_8)$alkyl (di)$(C_1$-$C_6)$alkylamine and their cosmetic salts and their solvates such as hydrates.

By $(C_{10}$-$C_{30})$alkylamido$(C_1$-$C_8)$alkyl (di)$(C_1$-$C_6)$alkylamine it must be understood that the alkyl group can be linear or branched, and by amido it must be understood the group —C(O)—N(R)— or —N(R)—C(O)— wherein R represents a hydrogen atom or a, linear or branched, $(C_1$-$C_6)$alkyl group. Particularly the $(C_{10}$-$C_{30})$alkylamido$(C_1$-$C_8)$alkyl(di)$(C_1$-$C_6)$alkylamine of the invention has the formula (A):

$$R^1\text{—C(O)—N(H)—}R^2\text{—}NR^3R^4 \quad (A)$$

wherein:
$R^1$ is a linear alkyl group having a $C_{10}$-$C_{30}$ carbon chain,
$R^2$ is a linear $C_1$-$C_6$ alkylene group, and
$R^3$ and $R^4$, same or different, are linear alkyl groups having a $C_1$-$C_4$ carbon chain.

Preferably in the formula (A),
$R^1$ is a linear alkyl group having a $C_{12}$-$C_{24}$ carbon chain,
$R^2$ is a linear $C_1$-$C_4$ alkylene group, and
$R^3$ and $R^4$ are same, representing methyl or ethyl groups.

More preferably, in the formula (A), $R^2$ is a —$(CH_2)_3$— group, and $R^3$ and $R^4$ are —$CH_3$ groups.

The cosmetic salts and the solvates such as hydrates of the tertiary substituted amidoamines are also used according to the present invention.

In view of improved conditioning effect, especially improved entangling of both wet and dry hair, under the context of the present invention, preferably the composition of the present invention comprises brassicamidopropyl dimethylamine of the following formula (A1):

$$\text{R—C(O)—N(H)—}(CH_2)_3\text{—}N(CH_3)_2 \quad (A1)$$

wherein R—C(O) is a fatty acid derived from *Brassica campestris* (rapeseed oil) seed oil, with a majority of behenyl $(C_{22})$ group.

As component brassicamidopropyl dimethylamine used in the composition of the present invention, mentions maybe made of PROCONDITION™ 22 from the company Inolex Chemical Company.

According to another embodiment, the $(C_{10}$-$C_{30})$alkylamido$(C_1$-$C_8)$alkyl (di)$(C_1$-$C_6)$alkylamine is stearylamidopropyl dimethylamine of the following formula (A2):

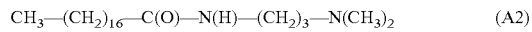

$$CH_3\text{—}(CH_2)_{16}\text{—C(O)—N(H)—}(CH_2)_3\text{—}N(CH_3)_2 \quad (A2)$$

As component stearylamidopropyl dimethylamine in the composition of the present invention, mentions may be made especially of TEGO® AMID S 18 from Evonik company and GENAMIN® SPA from Clarient company.

Preferably, the $(C_{10}$-$C_{30})$alkylamido$(C_1$-$C_8)$alkyl (di)$(C_1$-$C_6)$alkylamine and their cosmetic salts and their solvates such as hydrates is present in an amount in the range of from 0.1% to 8% by weight, based on the total weight of the composition.

In a preferable embodiment, the $(C_{10}$-$C_{30})$alkylamido$(C_1$-$C_8)$alkyl (di)$(C_1$-$C_6)$alkylamine is present in an amount ranging from 0.5% to 5% by weight, more preferably from 1% to 3% by weight in the composition of the present invention, based on the total weight of the composition.

(b) Dicarboxylic Acid Containing at Least One Hydroxyl Group not Bearing a Cyclic Group The composition of the present invention comprises at least one dicarboxylic acid containing at least one hydroxyl group, preferably two hydroxyl group, the said dicarboxylic acid not bearing a cyclic group.

Particularly, the dicarboxylic acid has a structure of formula (B) and its cosmetic salts and their solvates such as hydrates:

$$\text{HO—C—(O)-alk-C(O)—OH} \quad (B)$$

wherein alk represents a linear or branched, $(C_1$-$C_{10})$alkylene group substituted by at least one hydroxyl group, preferably substituted by two hydroxyl groups.

According to a preferred embodiment, the alk group represents a $(C_1$-$C_3)$alkylene group such as ethylene group substituted by at least one hydroxyl group, preferably substituted by two hydroxyl groups.

According to one preferred embodiment, the composition of the present invention comprises a dicarboxylic acid which is tataric acid of the formula (B1) and its cosmetic salts and their solvates such as hydrates:

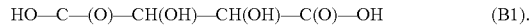

$$\text{HO—C—(O)—CH(OH)—CH(OH)—C(O)—OH} \quad (B1).$$

Such a dicarboxylic acid is commercially available, Mentions may be made, for example, E 334 NATURAL L+ TARTARIC ACID from GIOVANNI RANDI or VILLAPANA, NATURAL TARTARIC ACID from INDUSTRIA CHIMICA VALENZANA, and ACIDO TARTARICO from NERI.

Preferably, the at least one dicarboxylic acid containing at least one hydroxyl group, preferably two hydroxyl group as defined herein before is present in the composition of the present invention in an amount ranging from 0.01% to 5% by weight in the composition of the present invention, based on the total weight of the composition.

In a preferable embodiment, the above mentioned at least one dicarboxylic acid as defined herein before is present in an amount ranging from 0.1% to 2% by weight, more preferably from 0.2% to 1% by weight in the composition of the present invention, based on the total weight of the composition.

According to the preferred embodiment of the present invention, the composition comprises a salt obtained by neutralization reaction between the ingredient a) and the ingredient b), preferably between brassicamidopropyl dimethylamine and the dicarboxylic acid.

The amine and the acid are included in the composition at a level such that the molecule ratio of the brassicamidopropyl dimethylamine to the dicarboxylic acid is preferably from 1:5 to 10:1, more preferably from 1:5 to 5:1, most preferably 1:3 to 3:1.

(c) Oil(s) Selected from Ester of $C_6$-$C_{20}$ Fatty Acid and $C_6$-$C_{20}$ Fatty Alcohol The composition of the present invention comprises at least one oil selected from ester of $C_6$-$C_{20}$ fatty acid and $C_6$-$C_{20}$ fatty alcohol.

By "oil" it differs from the fatty substances such as pasty compounds or waxes in that the oils insoluble in water and are liquid at room temperature (25° C.) and at atmospheric pressure (760 mmHg or 1.013.105 Pa).

For the purposes of the present invention, the term "water-insoluble" refers to a compound whose solubility at spontaneous pH in water at 25° C. and at atmospheric pressure is less than 1% and preferably less than 0.5%.

According to the embodiment of the present invention, the oils used in the composition are esters of $C_6$-$C_{20}$ fatty acid and $C_6$-$C_{20}$ fatty alcohol.

More particularly, the oils are of plant origin. For example, the plant oils that comprise esters of fatty acid and fatty alcohol, or esters of fatty acid and fatty alcohol obtained from the plant oils.

According to an embodiment, the oil is a compound of formula (C):

R'—C(O)—OR"    formula (C)

wherein:
R' and R", same or different, represents a linear or branched, saturated or unsaturated $C_6$-$C_{20}$ carbon chain.

Preferably, the fatty acid that is suitable for the present invention includes caprylic acid, capric acid, lauric acid, myristic acid, stearic acid, or arachidic acid.

The fatty alcohol that is suitable for the present invention includes 3-methyl-3-pentanol, etchlorvynol, capryl alcohol, pelargonic alcohol, decyl alcohol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, or arachidyl alcohol.

Preferably in the formula (C), R' and R", same or different, represents a linear and saturated $C_6$-$C_{18}$ carbon chain.

Mentions of the compounds that are suitable for the composition of the present invention can be made of coco caprylate, coco caprate, sorbitan caprylate, sorbitan caprate, cetyl caprylate, hexadecyl decanoate, or a mixture thereof.

More preferably, in the formula (C), R' and R" are different from each other, wherein R' represents a linear and saturated $C_6$-$C_{14}$ carbon chain, and R" represents a linear and saturated $C_{10}$-$C_{18}$ fatty chain. Examples of the esters that are suitable for the present invention are, coco caprylate, coco caprate, or a mixture thereof.

Preferably, coco caprylate, coco caprate, or their mixture is used in the composition of the present invention.

Mentions may particularly be made of this type of ester oil, for example the product coco-caprylate/caprate sold under the tradename CETIOL® LC by the company BASF.

According to an embodiment, the oil is present in an amount ranging from 0.1% to 10% by weight, preferably from 0.1% to 5% by weight, more preferably from 0.1% to 3% by weight, relative to the total weight of the composition.

Additional Components

The composition of the present invention optionally comprises additional components which are conventionally used in conditioning the keratin fibers to provide various benefits. The additional components may be selected from cationic polymers, additional oils, and other additives.

Cationic Polymers

According to a preferred embodiment, the composition of the present invention may further comprise at least one cationic polymer.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and 5×106 approximately and preferably between 103 and 3×106 approximately.

There is no limitation on the types of cationic polymers that are suitable for the present invention. Mentions may be made of homopolymers or copolymers derived from acrylic or methacrylic esters or amides, cationic polysaccharides, polymers formed from piperazinyl units and divalent alkylene or hydroxyalkylene radicals containing straight or branched chains, water-soluble polyamino amides prepared in particular by polycondensation of an acidic compound with a polyamine, polyamino amide derivatives resulting from the condensation of polyalkylene polyamines with polycarboxylic acids followed by alkylation with bifunctional agents, polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, cyclopolymers of alkyldiallylamine or of dialkyldiallylammonium, quaternary diammonium polymers, polyquaternary ammonium polymers, quaternary polymers of vinylpyrrolidone and of vinylimidazole, polyamines, homopolymers or copolymers comprising one or more units derived from vinylamine and optionally one or more units derived from vinylformamide, or a mixture thereof.

Preferably, the composition of the present invention may further comprise, as a cationic polymer, at least one cationic polysaccharide.

Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are especially described in French patent 1 492 597, and mention may be made of the polymers sold under the name UCARE POLYMER "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group. Cationic cellulose copolymers or cellulose derivatives grafted with a water-soluble quaternary ammonium monomer are described especially in U.S. Pat. No. 4,131,576, and mention may be made of hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names CELQUAT L 200 and CELQUAT H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, chloride). Such products are especially sold under the names JAGUAR C13 S, JAGUAR C 15, JAGUAR C 17 or JAGUAR C162 by the company Rhodia (INCI: hydroxypropyl guar hydroxypropyltrimonium chloride).

When exists, the cationic polymer is present in an amount ranging from 0.001% to 10% by weight, preferably from 0.005% to 5% by weight, more preferably from 0.01% to 3% by weight, relative to the total weight of the composition.

Additional Oils

According to a preferred embodiment, the composition of the present invention may further comprise at least one additional oil, which is different from the ester oil as defined above.

The additional oils that can be used in the present invention are preferably hydrocarbon-based oils.

The term "hydrocarbon-based oil" is understood to mean oil essentially formed and even composed, of carbon and hydrogen atoms and optionally of oxygen and nitrogen atoms which does not comprise a silicone or fluorine atom; it can comprise ester, ether, amine and amide groups.

The oil may be volatile or non-volatile.

The term "non-volatile" means an oil of which the vapor pressure at 25° C. and atmospheric pressure is non-zero and is less than 0.02 mmHg (2.66 Pa) and better still less than 10-3 mmHg (0.13 Pa).

The term "volatile oil" means an oil of which the vapor pressure at 25° C. and atmospheric pressure is from 0.13 Pa to 40.000 Pa (0.001 to 300 mmHg) and preferably from 1.3 to 1300 Pa (0.01 to 10 mm Hg).

According to a preferred embodiment, the composition of the present invention comprises at least one oil selected from the group consisting of plant oil, fatty alcohols, or a mixture thereof.

In particular, the term "plant oil" means an oil as defined above, obtained from a species belonging to the plant kingdom.

As examples of plant oils that are suitable for the present invention, mentions maybe made of:
sweet almond oil,
argan oil,
avocado oil,
peanut oil,
*camellia* oil,
safflower oil,
calophyllum oil,
coconut oil,
colza oil,
copra oil,
coriander oil,
cucurbit oil,
wheatgerm oil,
jojoba oil or jojoba liquid wax,
linseed oil,
macadamia oil,
maize germ oil,
hazelnut oil,
walnut oil,
*vernonia* oil,
apricot kernel oil,
olive oil,
evening primrose oil,
palm oil,
passionflower oil,
grapeseed oil,
rose oil,
castor oil,
rye oil,
sesame oil,
rice bran oil,
soya oil, or soybean oil, and
sunflower oil.

Preferably, the composition of the present invention may further comprise at least one plant oil selected from apricot kernel oil, soya oil, or a mixture thereof.

Examples of fatty alcohols that can be used in the composition of the present invention include capryl alcohol, decyl alcohol, lauryl alcohol, myristyl alcohol, cetyl alcohol, stearyl alcohol, cetearyl alcohol, oleyl alcohol, or a mixture thereof.

The amount of additional oil(s), when they are present in the composition, preferably ranges from 0.01% to 20% by weight, better still from 0.05% to 10% by weight and more particularly from 0.1% to 5% by weight relative to the total weight of the final composition.

The composition of the present invention may comprise water, for example in a quantity of from 40 to 99% by weight, preferably from 50 to 98% by weight, most preferably from 55 to 95% by weight, relative to the total weight of the composition.

The composition according to the present invention may further comprise one or more additive(s) other than the compounds of the invention.

As additives that may be used in accordance with the invention, mention may be made of additional fatty substances, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, opacifiers, pearlescent or nacreous agents, antioxidants, hydroxyacids, fragrances and preserving agents.

The other additives may be selected conventionally by a person skilled in the art according to the practical demand.

According to a preferred embodiment, the present invention relates to a composition for conditioning keratin fibers, comprising, by weight relative to the total weight of the composition:

(a) from 1% to 3% by weight of brassicamidopropyl dimethylamine, stearylamidopropyl dimethylamine, or a mixture thereof;

(b) from 0.2% to 1% by weight of tartaric acid and their salts and solvates such as hydrates; and (c) from 0.1% to 3% by weight of at least one oil selected from coco caprylate, coco caprate, or a mixture thereof.

The keratin fibers conditioning composition of the present invention can be used in the form of rinse-off products or leave-on products, and can be formulated in a wide variety of product forms, including but not limited to creams, gels, emulsions, mousses and sprays. The composition of the present invention is especially suitable for after-shampoo conditioner.

The keratin fibers conditioning composition as described above may be used to condition the keratin fibers such as hair through conventional methods, depending on the application form of the composition.

For example, when used as an after-shampoo conditioner, the composition of the present invention may be applied through a method comprising following steps:
(i) after shampooing hair, applying to the hair an effective amount of the keratin fibers conditioning composition for conditioning the hair; and
(ii) rinsing the hair.

Still in another aspect, the present invention also relates to a use the association of (a), (b), and (c):
(a) at least one $(C_{10}\text{-}C_{30})$alkylamido$(C_1\text{-}C_8)$alkyl(di)$(C_1\text{-}C_6)$alkylamine and their cosmetic salts and their solvates such as hydrates, preferably stearylamidopropyl dimethylamine;
(b) at least one dicarboxylic acid containing at least one hydroxyl group, preferably two hydroxyl groups, the said dicarboxylic acid not bearing a cyclic group; and
(c) at least one oil selected from ester of $C_6\text{-}C_{20}$ fatty acid and $C_6\text{-}C_{20}$ fatty alcohol.

(a), (b), and (c) being used together for conditioning the keratin fibers, especially the hair.

The invention will be further illustrated by the following examples, which set forth particularly advantageous embodiments. While the Examples are provided to illustrate the present invention, they are not intended to limit it.

EXAMPLES

Following examples were prepared:

TABLE 1

| INCI | Invention formula | | Comparative formula | | |
|---|---|---|---|---|---|
| | 1 | 2 | A | B | C |
| Cetearyl alcohol (Lanette ® O from BASF) | 4.5 | 4.5 | 5.5 | 4.5 | 4.5 |
| Brassicamidopropyl dimethylamine (PROCONDITION ™ 22 from Inolex Chemical Company) ingredient (a) | 2 | 2 | 2 | 2 | 2 |
| Hydroxypropyl guar hydroxypropyltrimonium chloride (JAGUAR ® C162 from Rhodia) | 0.05 | 0 | 0 | 0 | 0 |
| Cetyl esters (and) cetyl esters (Radia 7747 RSPO MB from Oleon) | 0.5 | 0.5 | 0.5 | 0.5 | 0.5 |
| Coco-caprylate/caprate (CETIOL ® LC from BASF) ingredient (c) | 0.5 | 1 | 0 | 0 | 1 |
| Tartaric acid (ACIDO TARTARICO from NERI) ingredient (b) | 0.5 | 0.5 | 0.5 | 0.5 | 0 |
| Citric acid (Citric acid, anhydrous from Jungbunzlauer) | 0 | 0 | 0 | 0 | 0.5 |
| Apricot kernel oil (Refined Apricot Kernel oil from Olvea) | 0.5 | 0 | 0 | 0 | 0 |
| Caprylyl glycol | 0.3 | 0 | 0 | 0 | 0 |
| Soybean oil (Refined CN Soymean oil from Zor) | 1 | 0 | 0 | 0 | 0 |
| Isopropyl myristate (Isopropyl myristate from BASF) | 2 | 0 | 0 | 1 | 0 |
| Glycerin | 1 | 0 | 0 | 0 | 0 |
| water | added to 100 | added to 100 | added to 100 | added to 100 | added to 100 |

The above listed formulas were prepared according to known manufacturing method of cosmetic field.

The Comparative formulas A to C are in comparison with the Invention formula 2. Among which, Comparative formula A contains only cetearyl alcohol to replace the ingredient (c) according to the present invention; Comparative formula B contains isopropyl myristate instead of the ingredient (c) according to the present invention; Comparative formula C contains citric acid instead of the ingredient (b) according to the present invention.

Invention formula 1 is a hair conditioner product according to the present invention.

Dry Combing after Rinsing 0.4 g of the Invention formulas and Comparative formulas were applied on 6 g of slight damaged hair swatches, respectively, after shampooing of the hair swatches. The formulas were then left on the hair for 5 minutes. Then the hair is rinsed by warm water for 10 seconds, and left to dry over night at room temperature.

The friction force between the hair and a polyurethane pad was measured by the instrument named Texture Analyzer provided by Texture Technologies, Scarsdale, USA, before and after being treated with the conditioning composition, respectively. The friction force reduction percentage was calculated in accordance with the equation below:

$$\text{Reduction \%} = \frac{\text{Friction force before treatment} - \text{Friction force after treatment}}{\text{Friction force before treatment}} \times 100\%$$

Hair Sensory

The hair swatches used in dry combing test were then subject to hair sensory test. A panel of 5 experts gave scores to the smoothness of each hair swatch, at both wet and dry stage, after applying the invention and comparative formulas: 5 excellent, 4 very smooth, 3 smooth sensory, 2 poor, 1 very poor.

The results of the tests described above are listed in the table below

| Item | Invention formula | | Comparative formula | | |
|---|---|---|---|---|---|
| | 1 | 2 | A | B | C |
| Combing force reduction (dry combing) | 27.45% | 24.36% | 16.1% | 9.88% | 19.73% |
| Hair sensory (smoothness) | 4.4 | 4.2 | 3.2 | 2.8 | 3.2 |

It was observed from the results above, that comparing to the comparative formulas A to C, the invention formulas 1 and 2 provide improved disentangling to the hair, in particular to the dried hair. Besides, they both present improved hair sensory, such as smoothness, to the hair, comparing to the comparative formulas A to C.

The invention formula 1 shows a superior disentangling and hair sensory, and therefore is the preferred embodiment of the present invention.

The invention formulas 1 and 2 are stable after 2 months' storage.

The invention claimed is:

1. A composition for conditioning keratin fibers, comprising:
   (a) from 0.1% to 8% by weight relative to the total weight of the composition of brassicamidopropvl dimethylamine, stearylamidopropyl dimethvlamine, or a mixture thereof;
   (b) from 0.01% to 5% by weight relative to the total weight of the composition of tartaric acid;
   (c) from 0.1% to 10% by weight relative to the total weight of the composition of coco caprylate, coco caprate, or a mixture thereof; and
   (d) from 0.1% to 5% by weight relative to the total weight of the composition of cetyl alcohol, stearyl alcohol, or cetearyl alcohol.

2. The composition according to claim 1, wherein the ingredient (a) is brassicamidopropyl dimethylamine.

3. The composition according to claim 1, wherein the ingredient (a) is present in an amount ranging from 0.5% to 5% by weight relative to the total weight of the composition.

4. The composition according to claim 1, wherein the ingredient (b) is present in an amount ranging from 0.1% to 2% by weight relative to the total weight of the composition.

5. The composition according to claim 1, wherein the ingredient (c) is a mixture of coco caprylate and coco caprate.

6. The composition according to claim 1, wherein the ingredient (c) is present in an amount ranging from 0.1% to 5% by weight relative to the total weight of the composition.

7. The composition according to claim 1, further comprising at least one cationic polymer, selected from cationic polysaccharides.

8. The composition according to claim 1, wherein a mole ratio of (a):(b) is from 1:5 to 10:1.

9. A composition for conditioning keratin fibers, comprising, by weight relative to the total weight of the composition:
   (a) from 1% to 3% by weight of brassicamidopropyl dimethylamine, stearylamidopropyl dimethylamine, or a mixture thereof;
   (b) from 0.2% to 1% by weight of tartaric acid;
   (c) from 0.1% to 3% by weight of at least one oil selected from coco caprylate, coco caprate, or a mixture thereof;
   (d) from 0.1% to 5% by weight relative to the total weight of the composition of cetearyl alcohol, and
   (e) from 0.1 to 0.5% by weight of apricot kernel oil.

10. A method for conditioning keratin fibers, comprising application of the composition according to claim 1 to the keratin fibers.

11. The composition according to claim 1, further comprising at least one additional oil, different from ingredient (c), selected from the group consisting of plant oils, fatty alcohols, and a mixture thereof.

* * * * *